United States Patent [19]

Mosier

[11] Patent Number: 4,656,251

[45] Date of Patent: Apr. 7, 1987

[54] **RAPID SEPARATION OF *DIROFILARIA IMMITIS* IMMUNE COMPLEXES**

[75] Inventor: Larry D. Mosier, Creve Coeur, Mo.

[73] Assignee: Mallinckrodt, Inc., St. Louis, Mo.

[21] Appl. No.: 695,576

[22] Filed: Jan. 28, 1985

[51] Int. Cl.[4] .................... C07K 3/12; G01N 33/564
[52] U.S. Cl. .................................. 530/387; 530/413; 530/412; 530/829; 424/88; 424/85; 436/547; 436/538; 436/536; 436/507
[58] Field of Search ................ 424/88, 85; 435/7; 260/112 R, 112 B; 436/547, 538, 536, 506, 507

[56] References Cited

U.S. PATENT DOCUMENTS 2,469,193  5/1949  Cohen ............................ 260/112 B
2,725,235 12/1955  Rane ............................. 260/112 B
4,459,359  7/1984  Neurath ........................... 436/507

OTHER PUBLICATIONS

Jones et al., (Review article), "Isolation of Immune Complexes and Characterization . . . Human Disease", I Immunol. Methods, 44, (1981), pp. 249–270.

*Primary Examiner*—Morton Foelak
*Assistant Examiner*—Garnette D. Draper
*Attorney, Agent, or Firm*—Senniger, Powers, Leavitt and Roedel

[57] ABSTRACT

A method for the rapid separation of *Dirofilaria immitis* immune complexes in a sample of blood or bodily fluid from an animal infected with *Dirofilaria immitis* preparatory to assaying for the presence of circulating parasite antigens of *Dirofilaria immitis* involves the steps of (a) lowering the pH of the sample to below 3.0 to effect the separation of circulating parasite antigens of *Dirofilaria immitis* from antibodies therefor in the sample; (b) heating the sample to a temperature within the range of approximately 56° C. to 90° C. for a sufficient period of time to denature the separated antibodies; and (c) increasing the pH of the resulting sample to within the range of approximately 7 to 8 to produce a sample which may be assayed for the presence of circulating parasite antigens of *Dirofilaria immitis* without interference from the separated antibodies.

7 Claims, No Drawings

RAPID SEPARATION OF *DIROFILARIA IMMITIS* IMMUNE COMPLEXES

BACKGROUND OF THE INVENTION

This invention relates to diagnostic methods for the detection of *Dirofilaria immitis* antigens in blood or bodily fluid samples of infected animals and, more particularly, to improved means for achieving rapid separation of *Dirofilaria immitis* immune complexes in such samples preparatory to carrying out an assay for *Dirofilaria immitis* infection in animals, notably dogs.

Heartworm disease (dirofilariasis) is caused by *Dirofilaria immitis*, a filarial nematode parasite primarily of the dog, and is distributed throughout the world. While the parasite can cause heart failure, lung disease, disability and death, infected animals often have no outward evidence of disease. Signs of heartworm disease in dogs, when present, are nonspecific. The diagnosis of *D. immitis* infection is most commonly made by demonstrating microfilariae, larval forms of the parasite, in peripheral blood smears. However, this timehonored test is insensitive, and it is now well recognized that a significant proporti-on of infected dogs lack microfilaremia.

Recently, Weil (copending U.S. application Ser. No. 557,117, filed Dec. 1, 1983) and Weil et al., The Journal of Immunology, Vol. 134, No. 2, p. 1185-1191 February 1985) has identified circulating parasite antigens of *Dirofilaria immitis* present in the serum of *D. immitis* infected dogs and characterized the antigens to the extent necessary to distinguish these antigens from other antigens, and thereby render it possible to detect these specific antigens in the blood or bodily fluids of *D. immitis* infected animals. Weil has also produced and characterized monoclonal antibodies specific for such circulating *D. immitis* antigens and has developed a sensitive assay to detect parasite antigenemia in *D. immitis*-infected dogs. The assay involves providing a sample of blood or bodily fluid from an animal infected with or suspected of being infected with *Dirofilaria immitis* and assaying for the presence of the circulating parasite antigens of *Dirofilaria immitis* by means, for example, of a double antibody assay such as the sandwich ELISA assay in which a polyclonal antibody and a monoclonal antibody are used as the first and second antibodies.

Briefly, in one embodiment of the Weil assay, a rabbit polyclonal antibody directed towards the circulating parasite antigens of *Dirofilaria immitis* is attached to a solid support. The sample to be assayed and a horseradish peroxidase conjugated monoclonal antibody to the antigens is added to the solid support and allowed to react. If antigens are present in the sample, a polyclonal antibody-antigen-conjugated monoclonal antibody sandwich is formed which following addition of a horseradish peroxidase substrate will develop color. This color is subjectively or quantitatively compared to standards by the user and a determination of the presence or absence of the antigen is made.

One major problem in detecting circulating parasite antigens in accordance with Weil's assay is that the host's immunological response to the infection produces specific antibodies to the circulating antigens, thus forming immune complexes. These immune complexes are not detectable in some cases and must be separated in order to free the antigen of interest. In the above-noted Weil et al. publication, the method disclosed for freeing the antigens from the immune complexes involves the addition to the sample of 0.1 M disodium EDTA, pH 7.5, and heating to 100° C. for 5 minutes followed by centrifugation for 5 minutes at 16,000×G. Similarly, in Weil et al. Am. J. Trop. Med. Hyg. 33(3), 1984, p. 425-430, separation of the immune complexes involved the addition of 8% polyethylene glycol (PEG) in phosphate buffered saline (PBS) to a serum sample, incubation for 60 minutes at 4° C. and centrifugation at 16,000×G for 5 minutes. Similar procedures have been reported for separating complexes in the case of mycotic organisms (Weiner, Journal of Clinical Microbiology, Vol. 18 July, 1983, p. 136-142; Weiner et al., J. Lab. Clin. Med., Vol. 93, January, 1979, p. 111-119; and Weiner, Annals of Internal Medicine, 1980, 92:793-796). While these methods do effect separation of the immune complexes, the employment of higher temperatures such as 100° C. and/or centrifugation causes or tends to cause coagulation of the protein and therefore renders such methods inconvenient or impractical for routine use in veterinary clinics and the like.

There has been a need, therefore, for a rapid, practical, effective and convenient method for effecting separation of *Dirofilaria immitis* immune complexes in canine serum or other samples preparatory to assaying such samples for the presence of circulating antigens of *Dirofilaria immitis*.

SUMMARY OF THE INVENTION

Among the objects of the present invention may be noted the provision of a novel method for the rapid separation of *Dirofilaria immitis* immune complexes in a sample of blood or bodily fluid from an animal infected with *Dirofilaria immitis;* the provision of such a method which is convenient, practical and avoids the coagulation of protein in the sample; and the provision of a method of this type which results in the separated antibodies being substantially denatured so that they do not significantly recombine with the circulating parasite antigens of *Dirofilaria immitis* in the sample. Other objects and features will be in part apparent and in part pointed out hereinafter.

Briefly, the present invention is directed to a method for the rapid separation of *Dirofilaria immitis* immune complexes in a sample of blood or bodily fluid from an animal infected with *Dirofilaria immitis* involving the steps of (a) lowering the pH of the sample to below approximately 3.0 to effect the separation of circulating parasite antigens of *Dirofilaria immitis* from antibodies therefor in the sample; (b) heating the sample to a temperature within the range of approximately 56° C. to 90° C. for a sufficient period of time to denature the separated antibodies; and (c) increasing the pH of the resulting sample to within the range of approximately 7 to 8 to produce a sample which may be assayed for the presence of circulating parasite antigens of *Dirofilaria immitis* without interference from said separated antibodies.

DESCRIPTION OF THE PREFERRED EMBODIMENTS

In accordance with the present invention, I have found that the *Dirofilaria immitis* immune (antigen-antibody) complexes may be rapidly, conveniently and effectively separated without causing coagulation of the protein in the sample of blood or bodily fluid containing the immune complexes and without centrifugation. In the first step of the improved method of the invention, a sample of blood or bodily fluid from an animal infected with *Dirofilaria immitis* is treated to lower its pH to below approximately 3.0 to effect separation of the circulating parasite antigens of *Dirofilaria immitis* from antibodies therefor in the sample. To lower the pH below approximately 3.0 and achieve separation of the immune complexes, treatment of the sample with an acid material such as hydrochloric acid may be employed, but it is preferred to utilize an acid buffer such as 0.2M glycine, pH 0.85, containing 0.9% sodium chloride, or a solution of 50 mM glycine hydrochloride, pH 1.0, or other acid buffers, including glutamic acid or other organic acids, known to those in the art which will lower the pH to the required level to effect the desired separation of the immune complexes. Illustrative other buffer solutions which may be used are described in Remington's Practice of Pharmacy, Eleventh Edition.

The sample at this lowered pH level is then heated to a temperature of between approximately 56° C. to 90° C., preferably 56° C. to 70° C. and more preferably 60° C. to 65° C., for a sufficient period of time to denature the separated antibodies. It has been found that under these pH and temperature conditions, the antibody proteins are substantially denatured so that they cannot significantly recombine with the antigens to again form the immune complexes. Further, temperatures above approximately 90° C. tend to cause coagulation of the proteins and therefore are to be avoided. A heating or incubation period of at least approximately five minutes is generally sufficient to irreversibly denature the proteins and also contributes to a more rapid and practical separation technique for use on a clinical basis.

The sample is then treated or neutralized to increase the pH thereof to within the range of approximately 7 to 8 so as to produce a sample having the proper pH to be assayed for the presence of circulating parasite antigens of *Dirofilaria immitis* as, for example, by the improved assay of Weil referred to above. The sample may be neutralized to a pH within this desired range by the addition of base such as an alkali metal hydroxide (e.g. sodium hydroxide) although the addition of an alkaline buffer such as Tris (tris(hydroxymethyl)aminomethane), phosphate buffered saline, sodium borate or other such buffers known to the art is preferred. For example, the use of 0.3M Tris base containing 0.9% sodium chloride or 1.0M Tris together with a surfactant (e.g. "Brij 35" "Tween 20" or "Triton X100"), pH 10.5, has been found satisfactory.

The resulting sample having a pH of between 7 and 8 has thus been prepared for the detection of the circulating parasite antigens of *Dirofilaria immitis* without such antigens being bound up in the form of nondetectable immune complexes and without the antigens having been destroyed by the pretreatment of the sample in accordance with the present invention. The method of the invention achieves the rapid and convenient separation of *Dirofilaria immitis* immune complexes without the use of centrifugation and without coagulation of the proteins and thereby provides a relatively simple procedure which can be utilized clinically to produce samples which may be assayed without further processing.

The following examples illustrate the practice of the invention.,

Dog serum samples were treated with 0.2M glycine, pH 0.85, containing 0.9% NaCl. This mixture was then incubated at 56° C. for a minimum of 5 minutes, after which the mixture was neutralized using 0.3M Tris base containing 0.9% NaCl. The resulting sample was ready for assay to determine the presence of circulating parasite antigens of *Dirofilaria immitis*.

To 200 l of dog serum or plasma was added 200 l of 50 mM glycine HCl, pH 1.0, to decrease the sample pH to 2.0–2.5. The mixture was heated at 60°–70° C. for 5 minutes and then neutralized to pH 7.4–7.8 with 40 l (1 drop) of 1.0M Tris, 1.0% "Brij", pH 10.5. The sample so treated was ready for assaying.

Dog serum samples with high titers of anti-heartworm antibody were spiked with 40 ng/ml of purified heartworm antigen. These were then assayed with and without the pretreatment in accordance with the method of the invention and also with the pretreatment described above using EDTA, heating to 100° C. and centrifugation. The results are as follows:

| | Heartworm Antigen (ng/ml) | |
|---|---|---|
| 40 ng Spike No Treatment | 40 ng Spike Treatment of Present Invention | 40 ng Spike EDTA Treatment |
| 0 | 28(70)[a] | 21(53)[a] |
| 0 | 54(120) | 28(70) |
| 0 | 44(98) | 30(75) |
| 2 | 44(107) | 33(83) |
| 1 | 65(86) | 48(44) |
| 0 | 36(88) | 32(80) |

[a]Percent recovery of 40 ng spike

From the above, it will be seen that the method of the invention results in recoveries of 70–120% and is effective.

In view of the above, it will be seen that the several objects of the invention are achieved and other advantageous results attained.

As various changes could be made in the above compositions and methods without departing from the scope of the invention, it is intended that all matter contained in the above description shall be interpreted as illustrative and not in a limiting sense.

What is claimed is:

1. A method for the rapid separation of *Dirofilaria immitis* immune complexes in a sample of blood or bodily fluid from an animal infected with *Dirofilaria immitis* comprising the steps of
   (a) lowering the pH of said sample to below approximately 3.0 to effect the separation of circulating parasite antigens of *Dirofilaria immitis* from antibodies therefor in said sample;
   (b) heating said sample to a temperature within the range of approximately 56° C. to 90° C. for a sufficient period of time to denature the separated antibodies so that said denatured antibodies cannot significantly recombine with said antigens to again form immune complexes; and
   (c) increasing the pH of the resulting sample to within the range of approximately 7 to 8 to produce a sample which may be assayed for the presence of circulating parasite antigens of *Dirofilaria immitis* without interference from said separated antibodies.

2. A method as set forth in claim 1 wherein the pH is lowered in step (a) through the addition to the sample of an acid buffer.

3. A method as set forth in claim 2 wherein said acid buffer is glycine HCl.

4. A method as set forth in claim 1 wherein said sample is heated to a temperature of approximately 60°–65° C. in step (b).

5. A method as set forth in claim 1 wherein said sample is heated to a temperature within the range of approximately 56° C. to 90° C. for a period of approximately five minutes in step (b).

6. A method as set forth in claim 1 wherein the pH is increased in step (c) through the addition to said sample of an alkaline buffer.

7. A method as set forth in claim 6 wherein said alkaline buffer is tris(hydroxymethyl)aminomethane.

* * * * *